US008958866B2

(12) United States Patent
Bolar et al.

(10) Patent No.: US 8,958,866 B2
(45) Date of Patent: Feb. 17, 2015

(54) SYSTEM AND METHOD TO ANALYZE BLOOD PARAMETERS USING MAGNETIC RESONANCE IMAGING

(75) Inventors: Divya S. Bolar, Cambridge, MA (US); Elfar Adalsteinsson, Belmont, MA (US); Bruce R. Rosen, Lexington, MA (US); A. Gregory Sorensen, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 1073 days.

(21) Appl. No.: 12/413,349

(22) Filed: Mar. 27, 2009

(65) Prior Publication Data
US 2010/0030062 A1  Feb. 4, 2010

Related U.S. Application Data

(60) Provisional application No. 61/041,037, filed on Mar. 31, 2008.

(51) Int. Cl.
| | |
|---|---|
| *A61B 5/05* | (2006.01) |
| *G06K 9/00* | (2006.01) |
| *G01V 3/00* | (2006.01) |
| *A61B 5/055* | (2006.01) |
| *G01R 33/56* | (2006.01) |
| *G01R 33/563* | (2006.01) |
| *A61B 5/145* | (2006.01) |

(52) U.S. Cl.
CPC ............ *A61B 5/055* (2013.01); *G01R 33/5607* (2013.01); *G01R 33/56366* (2013.01); *A61B 5/145* (2013.01); *G01R 33/56316* (2013.01)

USPC ............ 600/419; 600/410; 382/128; 324/309

(58) Field of Classification Search
USPC ............ 600/407, 410, 419; 382/128; 324/309
See application file for complete search history.

(56) References Cited

U.S. PATENT DOCUMENTS

| | | | |
|---|---|---|---|
| 7,071,689 B2 * | 7/2006 | Golay et al. .................. | 324/309 |
| 7,545,141 B2 * | 6/2009 | Kimura ......................... | 324/306 |
| 2005/0277825 A1 * | 12/2005 | Wong et al. .................. | 600/410 |

FOREIGN PATENT DOCUMENTS

WO  WO 2006/127687  * 11/2006

OTHER PUBLICATIONS

Wong et al., "Velocity-Selective Arterial Spin Labeling", Magnetic Resonance in Medicine, 2006, 55:1334-1341.*

(Continued)

*Primary Examiner* — Katherine Fernandez
(74) *Attorney, Agent, or Firm* — Quarles & Brady, LLP

(57) ABSTRACT

A system and method for accurately producing MR images of selected vascular compartments includes employing a control scan and a tag scan, each including velocity selective modules that suppress signal from blood flowing faster than a given cutoff velocity, to acquire control and tag sets of NMR data that may be subtracted to produce a compartment-specific MR image that is substantially free of information from stationary tissues and blood outside the selective vascular compartments. Accordingly, physiological parameters, such as oxygen saturation ($SaO_2$), oxygen extraction fraction (OEF), and cerebral metabolic rate of oxygen ($CMRO_2$), can be generated from the compartment-specific images. Further still, kinetic curves of oxygen exchange can be created, thus providing detailed insight into oxygen exchange dynamics.

25 Claims, 9 Drawing Sheets

(56) References Cited

OTHER PUBLICATIONS

Hongyu An and Weili Lin, Journal of Cerebral Blood Flow and Metabolism (2000) 20:1225-1236.
Hongyu An, et al., NMR in Biomedicine (2001) 14:441-447.
Xavier Golay, et al., Magnetic Resonance in Medicine (2001) 46:282-291.
E. Mark Haacke, et al., Human Brain Mapping (1997) 5:341-346.
Xiang He, et al., Magnetic Resonance in Medicine (2007) 57:115-126.
Frank G. C. Hoogenraad, et al., Magnetic Resonance in Medicine (1998) 3997-107.
Yijun Liu, et al., Magnetic Resonance in Medicine (1999) 41:407-411.
Hanzhang Lu, et al., Magnetic Resonance in Medicine (2005) 53:808-816.
Joni M E Oja, et al., Journal of Cerebral Blood Flow & Metabolism (1999) 19, 1289-1295.
Peter C.M. Van Zijl, et al., Nature Medicine (1998) vol. 4, 2:159-167.

* cited by examiner

SYSTEM AND METHOD TO ANALYZE BLOOD PARAMETERS USING MAGNETIC RESONANCE IMAGING

CROSS REFERENCE TO RELATED APPLICATIONS

This application claims the benefit of U.S. Provisional Application 61/041,037, filed Mar. 31, 2008, which is incorporated herein in its entirety for all purposes.

STATEMENT REGARDING FEDERALLY SPONSORED RESEARCH

This invention was made with government support under 1R01EB007942-01A2 awarded by the National Institutes of Health. The government has certain rights in the invention.

FIELD OF THE INVENTION

The present invention relates to a system and methods for magnetic resonance imaging (MRI). More particularly, the present invention relates to targeting MRI signal from blood in specific vascular compartments using velocity selective pulses, accurately measuring oxygen saturation ($SaO_2$) from compartmentally-isolated MR signal, generating accurate oxygen extraction fraction (OEF) and cerebral metabolic rate of oxygen ($CMRO_2$) maps from the measurements, and generating kinetic curves of oxygen exchange to provide detailed insight into oxygen exchange dynamics.

BACKGROUND

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

In an effort to increase contrast attributable to the relatively small signal levels or weight particular signals attributable to cerebral blood flow (CBF) or another measurable mechanism, various "tagging" or "labeling" methods have been developed. One such method is referred to as the arterial spin labeling (ASL) family of techniques. These techniques have been used to detect and provide a quantitative measure of neuronal activity. In conventional ASL, arterial blood is tagged by magnetic inversion or saturation proximal to a region-of-interest (ROI) being imaged. That is, ASL techniques tag blood some distance away from the slice or volume-of-interest to be imaged. The tagged blood flows into the ROI and the inflow is detected as a modulation of the longitudinal magnetization.

To create an image of flow, most ASL methods acquire one image with tagged blood and one with untagged (control) blood. These two images are subsequently subtracted to generate a perfusion image. Because of the inherently low signal of a single perfusion image, a series of perfusion images is typically averaged to generate a mean perfusion image with an increased signal-to-noise ratio (SNR).

Beyond CBF, there are a number of clinically useful parameters related to blood. One clinically relevant feature of blood is oxygen saturation ($SaO_2$), from which oxygen extraction fraction (OEF) can be measured. Previous MR methods exist to measure OEF, but are limited. One class of methods attempts to measure the $SaO_2$ based on the $T_2$ (transverse) relaxation time of blood. The major challenge with such methods has been to separate the MR signal from various arterial, capillary, and venous compartments, whose blood will have different oxygen concentrations. For example, these methods are unable to cleanly target blood from post-capillary venules and cannot produce OEF maps on voxel-by-voxel basis. Instead, these methods have strict criteria for selecting voxels from which $SaO_2$ (and subsequently OEF) is measured.

Another class of methods exploits susceptibility differences between vessels and their surrounding tissue to determine venous $SaO_2$ ($Y_v$). Susceptibility methods are particularly limited as they require manual, visual identification of draining veins, as identified by a functional activation experiment. These methods also require precise knowledge of vessel geometry and cannot be used to generate absolute $Y_v$ or OEF maps.

A "static dephasing"-based approach has also been explored to produce both OEF and $CMRO_2$ maps. This approach, however, assumes random vessel orientation, no signal contributions from blood, and no diffusion effects. Moreover, the static-dephasing-regime theory used may not hold for capillaries.

Further still, there exists a multi-echo vascular occupancy (VASO) technique for estimating OEF. This technique requires prior estimates of baseline cerebral blood volume (CBV) and baseline $Y_v$ and, like other methods, only evaluates OEF for voxels activated during a neuroactivation task.

Thus, there have been several approaches proposed to measure $SaO_2$ and OEF. However, these approaches are hindered by restrictive assumptions, are confounded by signal arising from tissue, and/or are unable to produce accurate OEF maps on a voxel-by-voxel basis.

It would, therefore, be desirable to have a system and method capable of accurately isolating signal from specific vascular compartments, measuring $SaO_2$, and generating accurate OEF and $CMRO_2$ maps on a voxel-by-voxel basis.

SUMMARY OF THE INVENTION

The present invention overcomes the aforementioned drawbacks by providing a system and method for accurately measuring $SaO_2$ directly from compartmentally-isolated blood using magnetic resonance imaging. Furthermore, the present invention is able to generate accurate OEF and $CMRO_2$ maps from the measurements, since $SaO_2$ is an intrinsic property of blood alone. Further still, the present invention is able to generate kinetic curves of oxygen exchange, thus, giving detailed insight into oxygen exchange dynamics.

One aspect of the invention provides an ability to isolate blood signal based on velocity range and acceleration. Velocity and acceleration are properties of blood that are dependent on the containing vascular compartment. A velocity range defines a specific population of blood; however, for all but capillary blood, a velocity range selects an arterial pool of blood and the analogous venous pool. The present invention allows discrimination between the two based on the fact that arterial blood decelerates as it approaches the capillaries, while venous blood accelerates while approaching larger veins. Thus, the combination of a delay (inflow time) framed by velocity selection modules, allows targeting of blood that either decelerates (i.e. arterial blood) or accelerates (i.e. venous blood). In this way, it is possible to specifically target arterial/arteriolar or venous/venular blood compartments, despite similar velocity range. Additionally, since stationary spins are eliminated by control-tag subtraction, signal is clearly attributed to spins originating in blood. Because of the precision targeting of arteriolar and venular blood signal, OEF (and subsequently $CMRO_2$) can be measured on a voxel-by-voxel basis.

Another aspect of this invention exploits the unidirectional nature of blood flow in human physiology (i.e. blood flows from arteries, through capillaries, into veins). By appropriately using velocity selection and cycling through different inflow times, it is possible to target a bolus of blood at different stages of its traversal through late arteriolar and capillary bed vasculature. Since oxygen exchange occurs from blood to tissue during this traversal, subsequent $SaO_2$ measurements allow the generation of oxygen saturation curves and the characterization of oxygen exchange dynamics.

Various other features of the present invention will be made apparent from the following detailed description and the drawings.

DESCRIPTION OF THE PREFERRED EMBODIMENT

Figure 1:
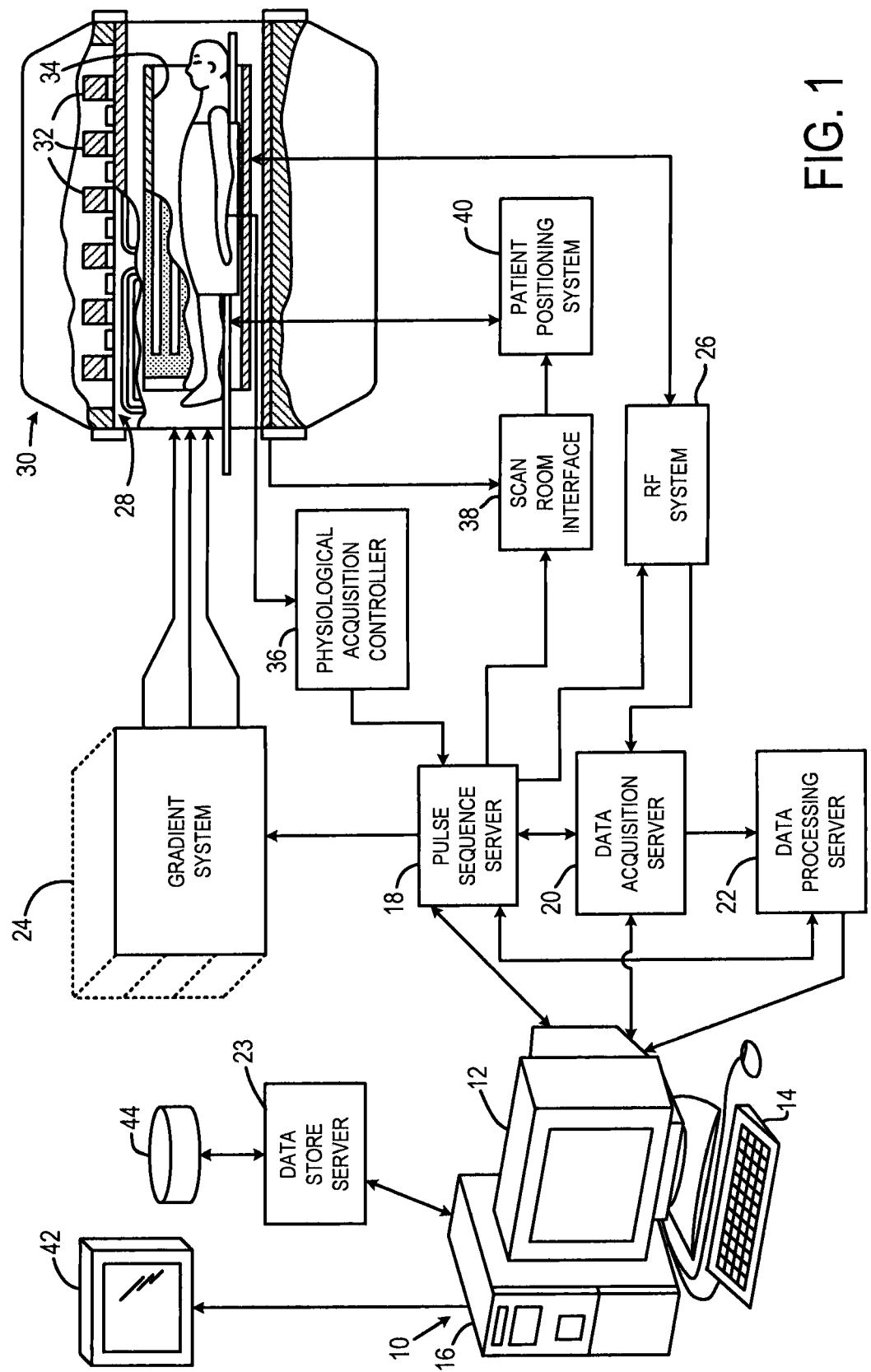
FIG. 1 is a block diagram of an MRI system that employs the present invention.

Referring particularly to FIG. 1, the present invention is employed using an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers: a pulse sequence server 18; a data acquisition server 20; a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$, and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi=\tan^{-1}Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
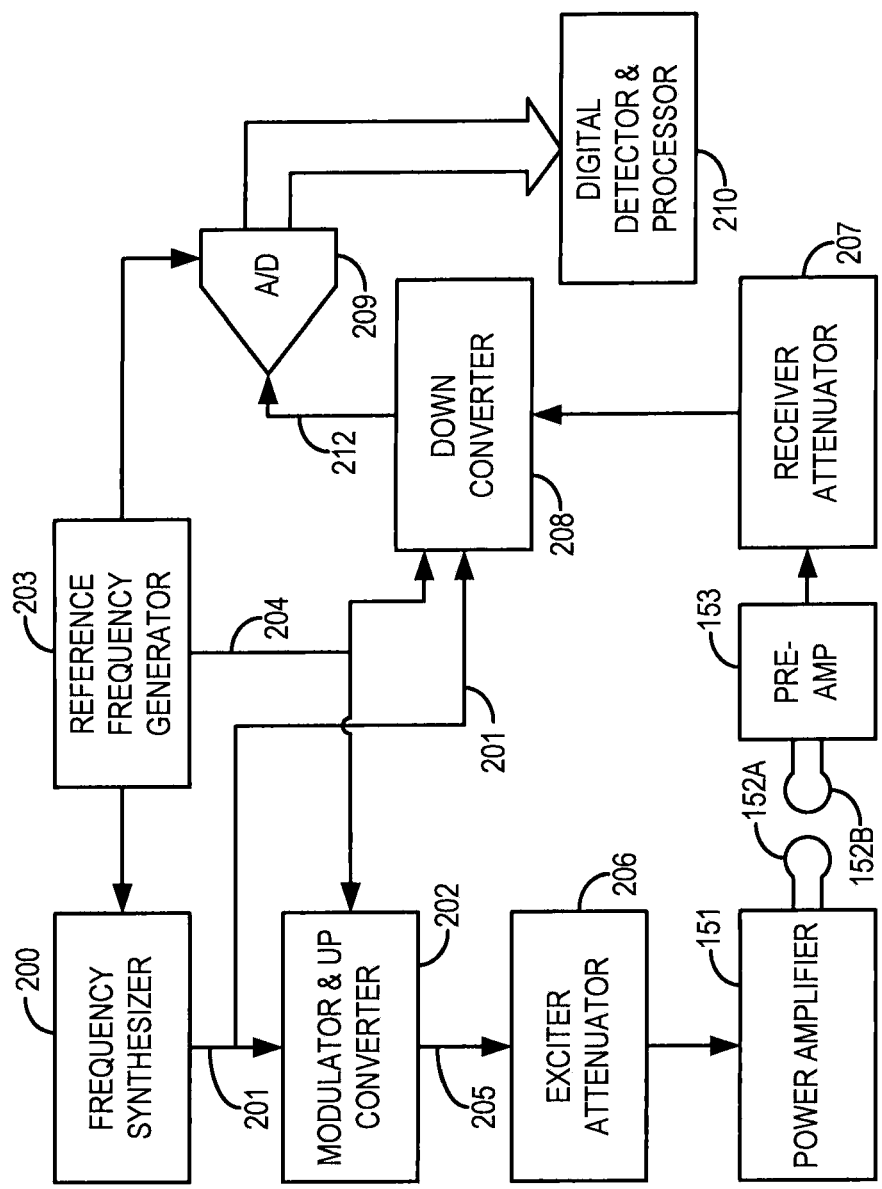
FIG. 2 is a block diagram of an RF system that forms part of the MRI system of FIG. 1.

As shown in FIG. 1, the RF system 26 may be connected to the whole body RF coil 34, or as shown in FIG. 2, a transmitter section of the RF system 26 may connect to one RF coil 152A and its receiver section may connect to a separate RF receive coil 152B. Often, the transmitter section is connected to the whole body RF coil 34 and each receiver section is connected to a separate local coil 152B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 152A.

Referring still to FIG. 2 the signal produced by the subject is picked up by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the MR signal with the carrier signal on line 201 and then mixes the resulting difference signal with a reference signal on line 204. The down converted MR signal is applied to the input of an analog-to-digital (A/D) converter 209 that samples and digitizes the analog signal and applies it to a digital detector and signal processor 210 that produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

As will be described, using the above-described system, the present invention provides a technique to isolate signal from specific blood compartments. The isolated signal is subsequently used to measure fundamental properties of brain physiology. The technique specifically employs velocity-selective spin saturation to target signal from distinct vascular compartments (e.g. arteriolar, venular, capillary), based on differences in blood velocity and acceleration. Oxygen saturation ($SaO_2$), a compartment-specific physiological parameter, is then measured and used to calculate oxygen extraction fraction (OEF), cerebral metabolic rate of oxygen ($CMRO_2$), and oxygen exchange dynamics, on voxel-by-voxel basis.

Figure 3:
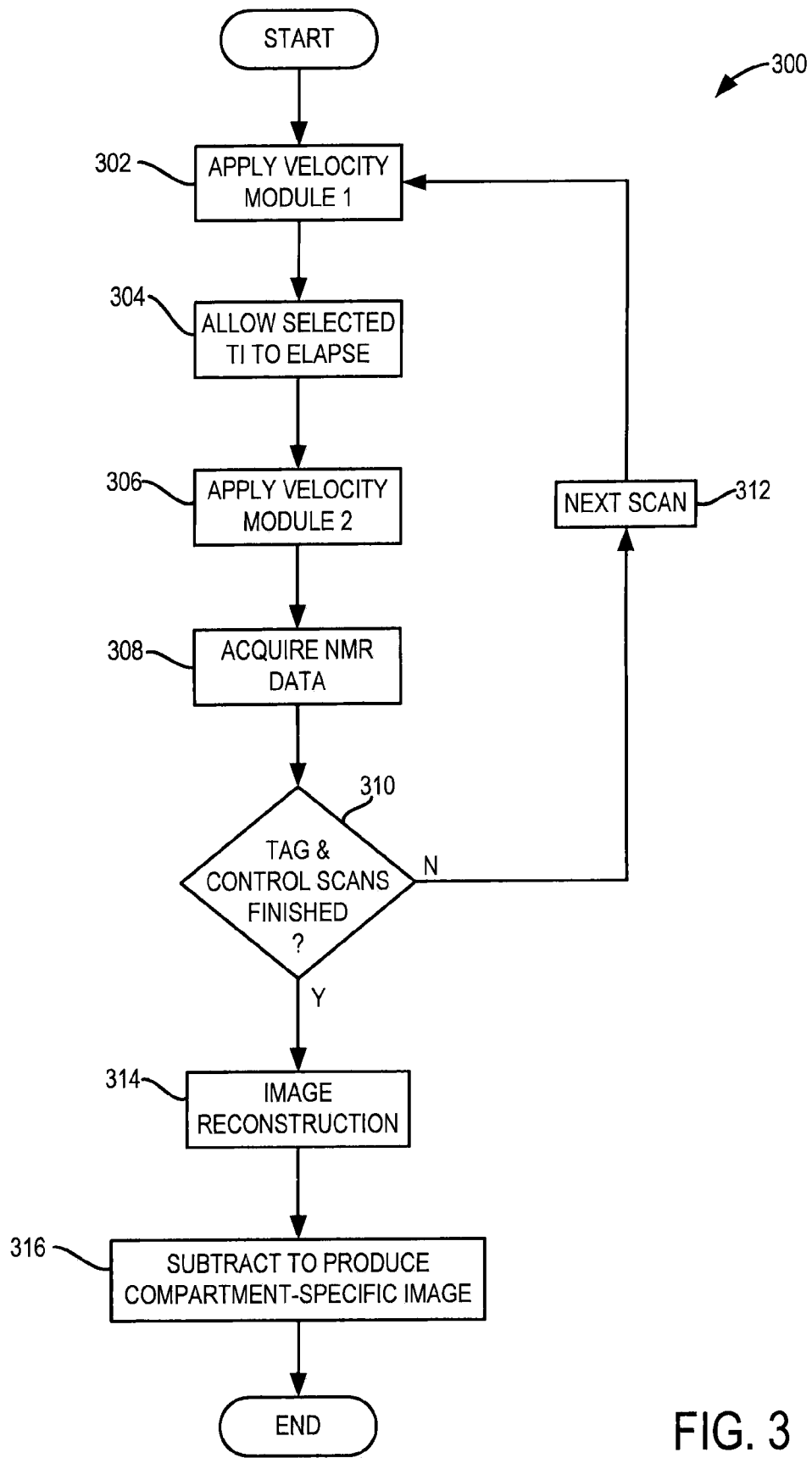
FIG. 3 is a flowchart setting forth the steps of a method for producing a compartment-specific image in accordance with the present invention.
Figure 4:
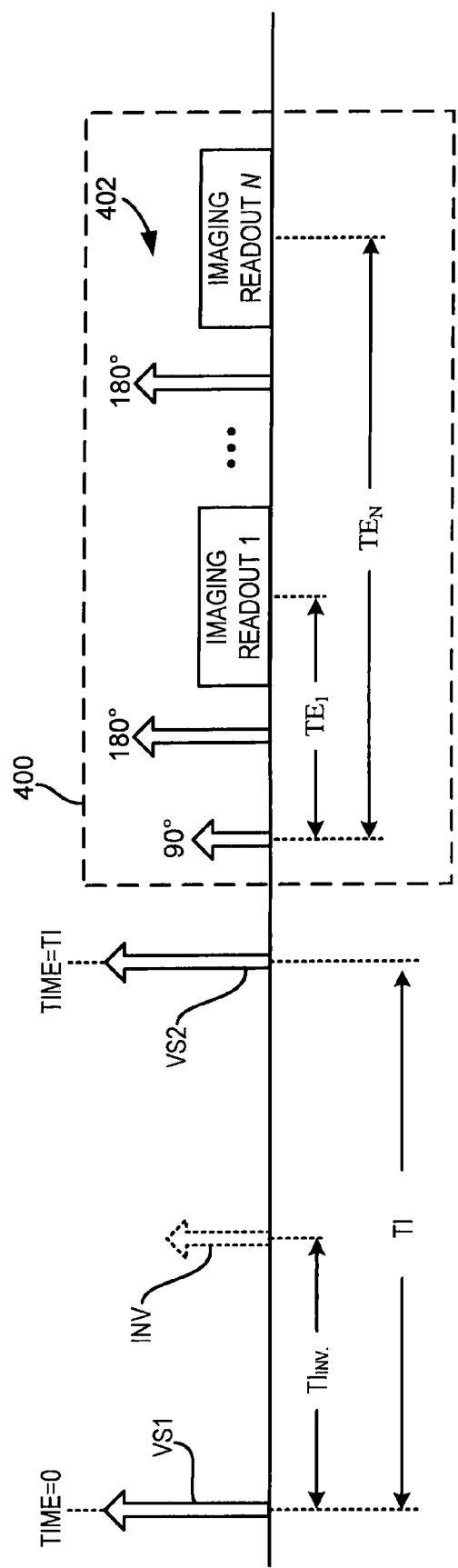
FIG. 4 is a pulse sequence diagram for vascular compartment signal targeting shown with multi-echo, spin echo imaging module in accordance with the present invention.

Referring to FIGS. 3 and 4, a general method for isolating NMR signal from specific blood compartments and a simplified pulse sequence diagram are provided. The method employs a separate tag scan and control scan to perform compartment-specific NMR signal isolation. The tag scan begins with the velocity-weighted image acquisition process indicated generally at 300. This process includes applying a spatially non-selective, velocity-selective pulse train VS1 to the entire imaging volume at process block 302. Before VS1, all blood spins in the subject being imaged (for example, arterial, capillary, venous) is relaxed. Application of VS1 suppresses signal from blood flowing faster than a selected cutoff velocity via saturation. At process block 304, a selected delay time, or "inflow time" (TI), is allowed to elapse, during which remaining blood spins flow into various vascular compartments. A second velocity-selective module VS2 is then applied at process block 306 to eliminate blood spins flowing faster than second selected velocity. This suppresses spins that have accelerated above the cutoff velocity during the TI, for example, blood spins entering the venous vasculature from the capillaries. It is contemplated that VS2 may include a $T_2$ preparation module, which employs additional pulses to allow for $T_2$ weighting. The effective echo time (TE) can be controlled by varying the number of additional pulses.

Following the velocity-selective modules, an imaging module, indicated generally at 400, is applied at process block 308 to acquire the tag NMR data set. For example, a series of N NMR images at N different echo times may be acquired using the depicted $T_2$-weighted, multi-echo acquisition scheme 402 that includes an initial 90 degree RF pulse followed by a series 180 degree RF pulses and imaging readouts at times $TE_N$. Alternatively, an echo planar (EPI) imaging module may be employed with the above-described $T_2$ preparation module to acquire NMR data from which a single MR image having a selected TE can be produced. If, at decision block 310, both tag and control NMR data sets have not been acquired, then the system proceeds to the control scan at process block 312 and acquires the control NMR data set using the velocity-weighted image acquisition process 300. However, the selected cutoff velocities for both VS1 and VS2 can vary between the tag and control scans, as different combinations of selected cutoff velocities and TI allow NMR signals from different compartments to be isolated. This "compartmental spin-targeting" will be further described below.

The acquired tag and control NMR data sets are reconstructed at process block 314 to produce separate tag and control MR images. For example, if the $T_2$-weighted, multi-echo image acquisition scheme 402 were performed, the image reconstruction process would produce a series of $T_2$-weighted images at N different echo times for both the tag NMR data set and the control NMR data set. It is estimated that a series of such images having sufficient signal-to-noise ratio (SNR) may be acquired in five to six minutes using a current, commercially-available MR scanners. Likewise, scans employing the above-described EPI imaging module can be performed repeatedly with different $T_2$ preparation modules to produce a series of $T_2$-weighted images. At process block 316, the subtraction of the tag images from the control images produces compartment-specific MR images, wherein both moving blood spins outside the compartment-of-interest and stationary spins are substantially eliminated. It should be noted that the control scan and tag scan may be performed in any order, not just that prescribed above. Likewise, the subtraction of tag and control NMR data sets may alternately be performed prior to image reconstruction.

In addition, by employing additional velocity selection in the VS2 module of the control scan, the present invention can allow "velocity bracketing." That is, the targeting of compartmental blood in a specific velocity range can be performed, thereby adding an additional level of constraint to the targeted blood. Velocity bracketing can, for example, substantially eliminate signal from larger veins while preserving signal in smaller venules. This is especially beneficial for regions containing a high density of draining veins, for example, the visual cortex. Velocity bracketing can, for example, improve the likelihood that oxygen saturation changes are measured only from PCV blood, regardless of vessel-type within a voxel or inflow time (TI) used. Velocity bracketing can also provide improved spatial accuracy in fMRI studies employing the present invention, as changes in PCV oxygen saturation are tightly localized to regions immediately distal to neuronal activation.

The production of compartment-specific MR images outlined above with reference to FIGS. 3 and 4 can be complicated by $T_1$ relaxation. That is, spins suppressed by VS1 may experience recovery as TI progresses. The recovered signals may be acquired by the imaging module and spins from unwanted compartments will contribute to the acquired tag and/or control NMR data sets. Without compensation, these unwanted spins may not subtract completely, resulting in MR images with reduced compartmental-specificity. The present invention may therefore include an inversion pulse (IR) at time $TI_{INV}$ to null recovering signal, so spins in this unwanted population are saturated in the tag and/or control scans at time TI and the imaging modules acquires reduced amounts of undesired signals. For example, more accurate targeting of blood from compartments on the venous side of the circulatory system is typically provided by such an inversion pulse.

The following table, text, and diagrams illustrate how different parameter combinations can be used to target three different vascular compartments and how compartment-specific MR images can subsequently be employed to measure physiologic properties.

TABLE 1

Example cutoff velocities that can be used to measure physiological parameters.

| Compartment Targeted | Cutoff Velocity (cm/s) | | | | Allows Measurement of: |
|---|---|---|---|---|---|
| | VS Module I: Control | VS Module I: Tag | VS Module II: Control | VS Module II: Tag | |
| Venules | 1 | 1 | NONE | 1 | $SaO_2$, OEF, $CMRO_2$ |
| Arterioles | 6 | 4 | 4 | 4 | $SaO_2$, OEF, $CMRO_2$ |
| Late arterioles/ capillaries | 4 | 1 | 1 | 1 | $SaO_2$, $O_2$ exchange dynamics |

Different subpopulations (as defined by disease or age, for example) require different values of the various cutoff velocities, but in all cases, the method can be adapted to yield the desired physiological parameters.

Figure 5:
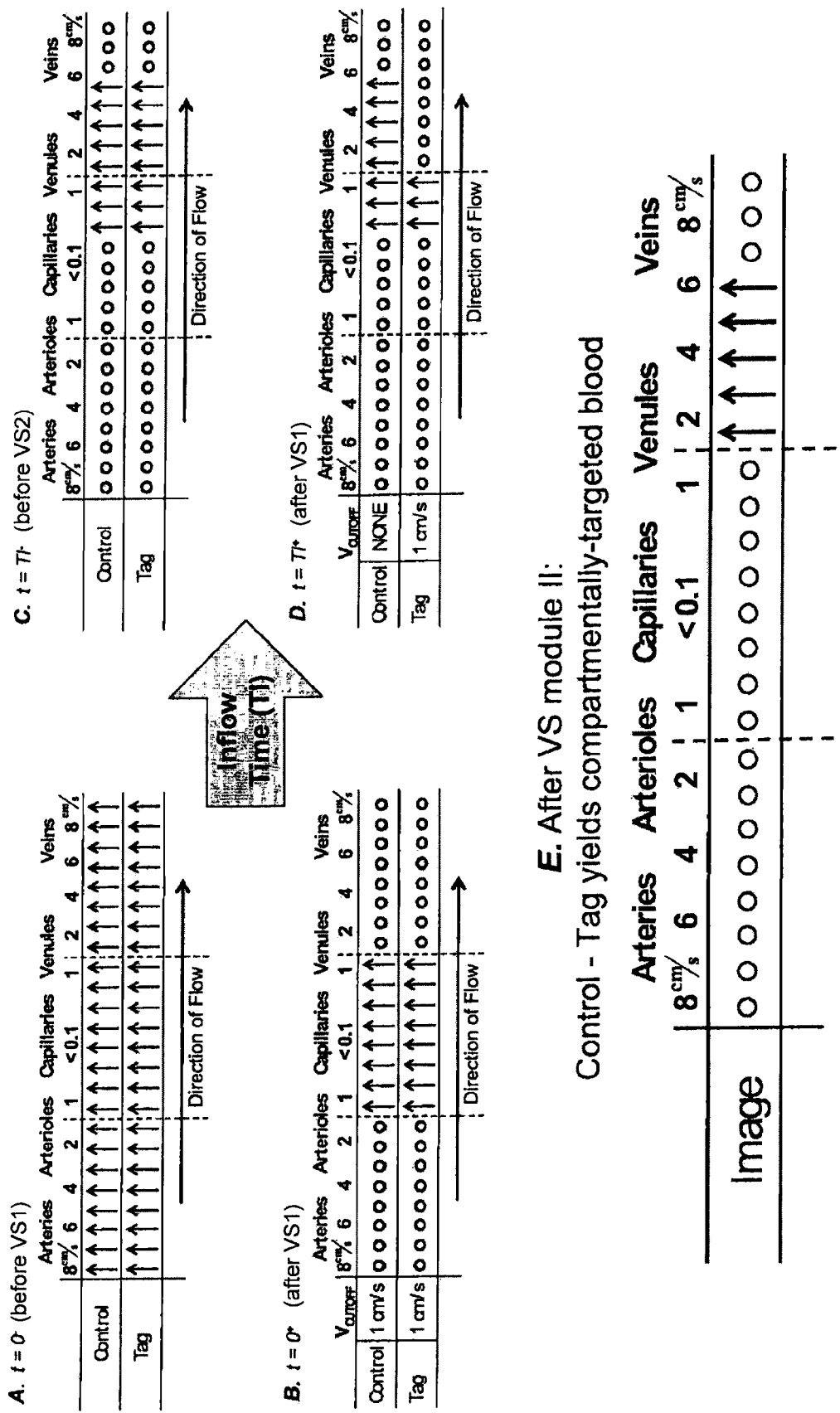
FIG. 5 is a detailed schematic illustrating how the technique of the present invention can be used to target low-velocity, post-capillary venular blood.

Referring now to FIG. 5, a detailed schematic is provided to illustrate the application of the above-described method in targeting spins from low-velocity, post-capillary venular blood. In FIG. 5, relaxed spins are denoted by upright arrows (↑) and saturated spins by hollow circles (○). Dotted vertical lines correspond to a 1 cm/s blood velocity, that is, the cutoff velocity in parts B and D.

At time=0, before the first velocity-selective module (VS1) is applied, spins in all blood compartments are relaxed, as denoted by the upright arrows in part A. For both the tag and control experiments, a high degree of velocity weighting is applied during VS1. In this example, as indicated in part B, the cutoff velocity ($V_{CUTOFF}$) is set to 1 cm/s to select for slow moving spins in capillaries and small arterioles/venules, while saturating the faster moving spins found in larger vessels. Following the application of VS module I, a user-specified delay inflow time (TI) elapses, allowing targeted spins to flow out of the selected compartments and into the venular vasculature, as indicated in part C. Immediately after TI, but before the second velocity selective module (VS2), some spins will invariably remain in the capillary bed. The second velocity selective module is then applied with different cutoffs for the tag and control scans. The control experiences no velocity weighting and preserves the spin configuration prior to VS2, while the tag experiences the same velocity weighting used in VS1, in this case 1 cm/s. Part D shows the resultant spin configurations for both tag and control scans. For each scan, imaging acquisition immediately follows VS2 to produce two sets of images that yield the final magnetization described in part E when subtracted. If the $V_{CUTOFF}$ and TI are chosen correctly, for example, using the appropriate values from Table 1, only blood in venular compartments will contribute to the final signal.

As mentioned above, the primary parameters under user control are inflow time TI and the four velocity weighting factors ($V_{CUTOFF}$). Different combinations of these parameters can result in different types of compartmental targeting. The above-described sequence results in post-capillary venule (PCV) signal targeting, but other combinations can result in greater flexibility by offering different types and degrees of compartmental targeting.

Figure 6:
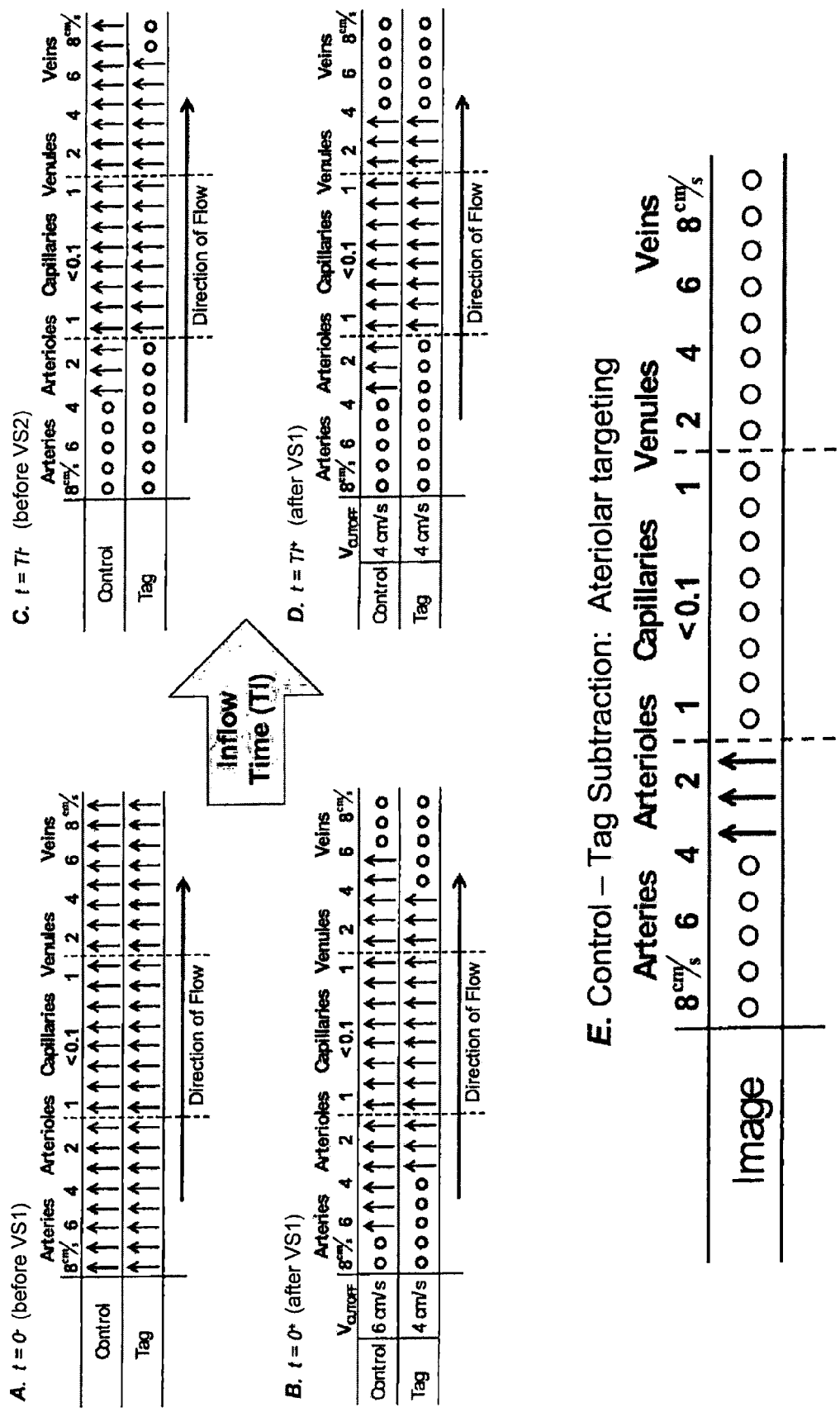
FIG. 6 is a detailed schematic illustrating how the technique of the present invention can be used to target arterial/arteriolar blood.

For example, referring now to FIG. 6, an adjusted combination of parameters can be used to target late-arterial/arteriolar blood. Again, relaxed and saturated spins are respectively denoted by upright arrows (↑) hollow circles (○). Dotted vertical lines correspond to a 1 cm/s blood velocity. In this case, the following parameter combination can result in the targeting of arterial/arteriolar blood: $V_{CUTOFF}$=6 cm/s for VS1 in the control scan; $V_{CUTOFF}$=4 cm/s for VS1 in the tag scan; and $V_{CUTOFF}$=4 cm/s for VS2 in both the control and tag scans. Parts A-D depict the dynamic spin diagrams for the control and tag scans at different stages of the velocity-weighting process. Part E depicts the final arteriolar-weighted signal resulting from control-tag subtraction.

Figure 7:
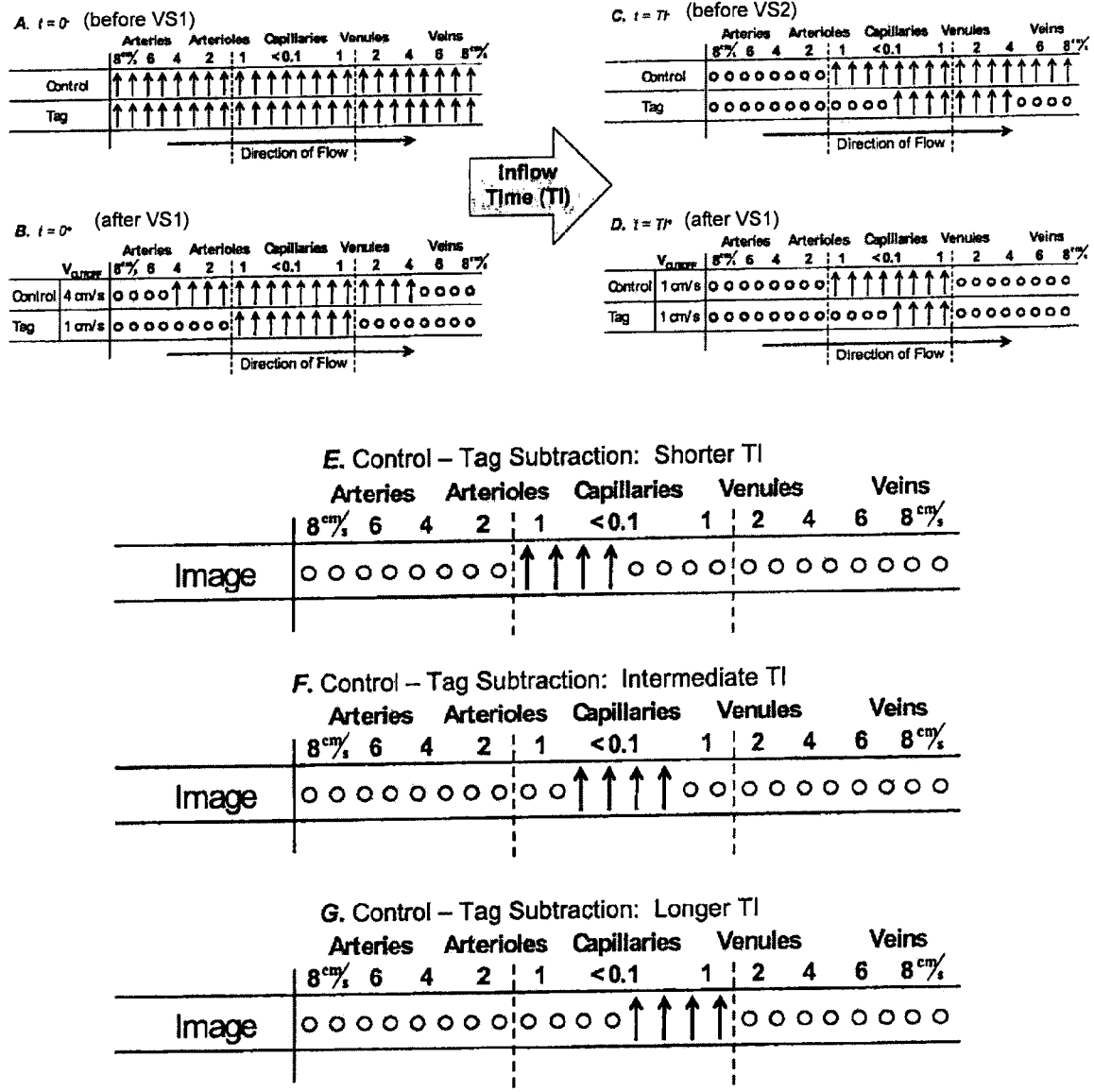
FIG. 7 is a detailed schematic illustrating how the technique of the present invention can be used to target capillary and/or late arteriolar blood.

Similarly, referring to FIG. 7, yet another parameter combination can result in targeting of capillary and/or late arteriolar blood, that is, blood that has started exchanging oxygen with surrounding tissue. In this case, $V_{CUTOFF}$=4 cm/s for VS1 in the control scan; $V_{CUTOFF}$=1 cm/s for VS1 in the tag scan; and $V_{CUTOFF}$=1 cm/s for VS2 in both the control and tag scans. Parts A-D show the dynamic spin diagram, and Parts E to G show final signal after control-tag subtraction for NMR data acquired using three different TI's. The use of multiple TI's in this case illustrates the present invention's ability to isolate blood spins at different points as they traverse the capillary bed. This is especially useful as it allows targeting of blood volumes that have experienced different amounts of gas exchange and thus have different degrees of oxygen saturation. However, care should be taken with this approach. As TI increases, spins initially in capillaries will exchange with those in surrounding tissue. If TI is too long, spins from tissue beds will contribute significantly towards the MR acquired signal, which, accordingly, will no longer be confined to the vascular compartment.

Figure 8:
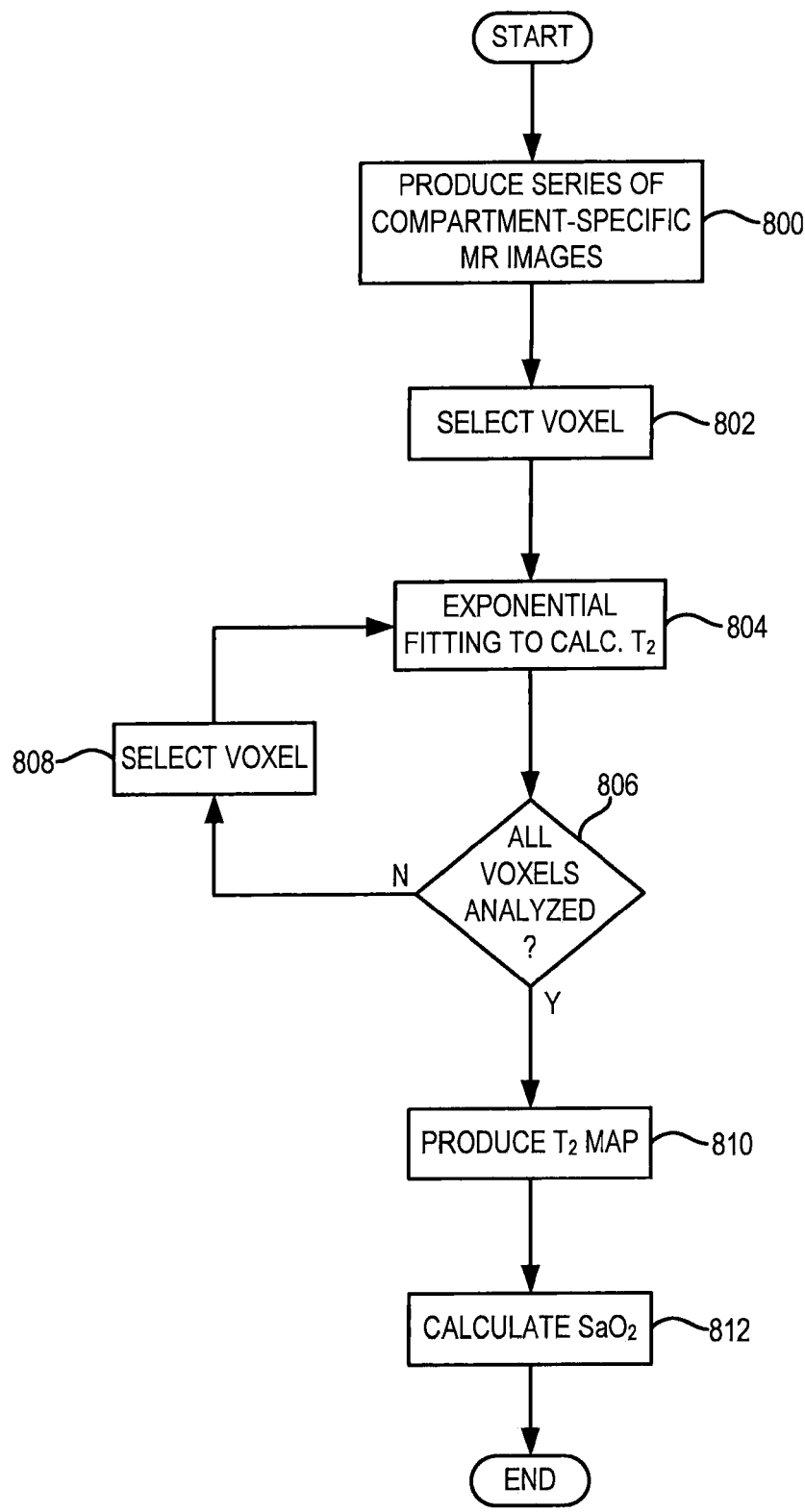
FIG. 8 is a flowchart setting forth the steps of calculating physiological parameters from the saturation of oxygen ($SaO_2$) in accordance with the present invention.

Referring now to FIG. 8, the present invention may be employed to measure fundamental physiological parameters such as blood oxygen saturation ($SaO_2$), oxygen extraction fraction (OEF), and blood pH, which can be determined for specific vascular compartment using a pH imaging module. An exemplary measurement of compartmental blood $SaO_2$, a key physiological parameter, begins at process block 800 with the production of a series of compartment-specific MR images at different echo times by employing the present invention and the above-described T2-weighted, multi-echo imaging scheme. It can be assumed that images arising from different echo times will effectively contain blood from the same vascular compartment so long as there are not too many echoes and the difference in echo times is small, for example, on the order of tens of milliseconds. At process block 802, corresponding voxels in the series of images may be selected and then, at process block 804, a $T_2$ value can be calculated by exponentially fitting the corresponding MR data from different echo times. This method then cycles to remaining voxels at process block 808 until, at decision block 806, it is determined that $T_2$ values have been calculated for all appropriate voxels. At process block 810, a $T_2$ map is generated and compartmental $SaO_2$ is calculated from the $T_2$ map at process block 812 via, for example, empirically determined calibration curves or known calculations described in van Zijl P C, Eleff S M, Ulatowski J A, Oja J M, Ulug A M, Traystman R J, Kauppinen R A. Quantitative assessment of blood flow, blood volume and blood oxygenation effects in functional magnetic resonance imaging. Nat Med 1998; 4(2):159-167. The separation of MR signal from various arterial, capillary, and venous vascular compartments, each having different oxygen concentrations, had previously been a challenge in effectively implementing the method of van Zijl et al. Accordingly, the present invention allows precise targeting of blood signal from a specific vascular compartment.

Going a step further, it is possible to estimate a partial pressure of oxygen ($PO_2$) from $SaO_2$ using the oxyhemoglobin dissociation curve described, for example, by Berne R M LM. Physiology. St. Louis: Mosby Year Book; 1993. By measuring both arteriolar SaO2 ($Y_a$) and venular SaO2 ($Y_v$) using the approaches illustrated in FIGS. 5 and 6, oxygen extraction fraction (OEF) is calculated as:

$$OEF = \frac{Y_a - Y_v}{Y_a}.$$

A fundamentally important and physiologically-relevant is the cerebral metabolic rate of oxygen ($CMRO_2$), which is an indicator of tissue viability and function. Using the above-described approaches, that is, compartmental targeting and multi-echo $T_2$ measurement, $CMRO_2$ can be calculated on a voxel-to-voxel basis, using the following equation to effectively create an absolute $CMRO_2$ map:

$$CMRO_2 = (Y_a - Y_v) \times [Hb_{tot}] \times CBF;$$

where [$Hb_{tot}$] is the total concentration of hemoglobin in the blood, which is directly related to the hematocrit. Normal cerebral hematocrit values can be taken from the literature or measured directly from a small blood sample via finger prick and quantitative cerebral blood flow (CBF) can be measured using well-known arterial spin labeling (ASL) MR techniques.

Figure 9:
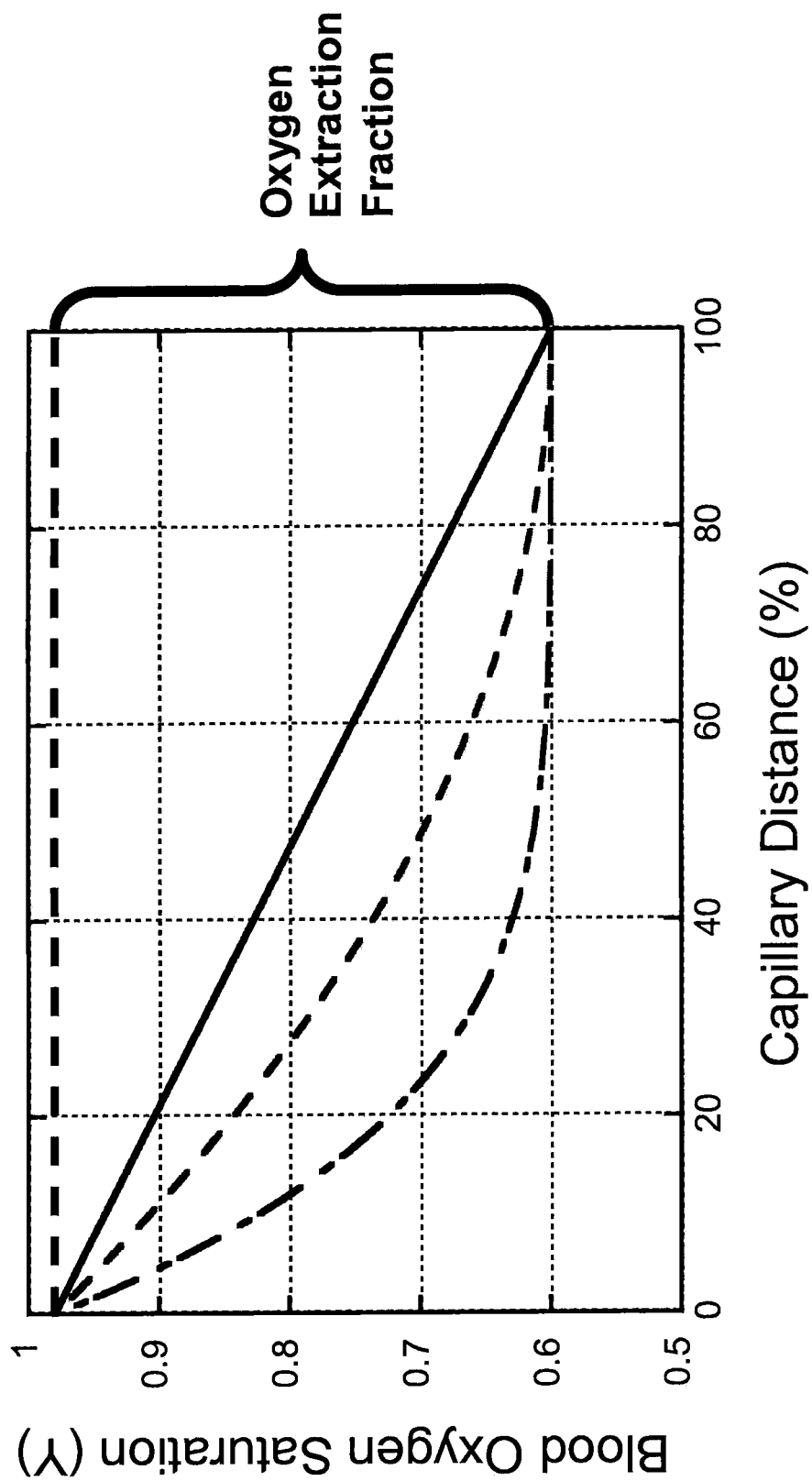
FIG. 9 is a graph showing that two capillary beds could have completely different exchange dynamics, but the same overall OEF.

Referring to FIG. 9, specific velocity-weighting combined with multiple inflow times, as indicated in FIG. 7, Parts E to G, can be employed to target a blood bolus as it traverses the small arteriole network and capillary bed. $SaO_2$ maps at these individual TI's allow investigation of oxygen exchange kinetics by providing $SaO_2$ measurement at different regions along the capillary length. Going a step further, the present invention allows the measurement of oxygen exchange dynamics on a voxel-by-voxel basis. While OEF measurements give the total percent of oxygen extracted as blood traverses the smaller vascular beds, they provides no information about the rate of exchange or exchange dynamics. In other words, two capillary beds could have completely different exchange dynamics, but share the same overall OEF. This phenomenon is highlighted in FIG. 9.

Specifically, FIG. 9 shows sample kinetic curves of oxygen saturation as a function of capillary position. Exchange dynamics can vary significantly, while still yielding the same oxygen extraction fraction (OEF). The solid curve describes a linear relationship between saturation and capillary distance, while the dashed and dotted-dashed curves show more exponential-like relationships. That is, the solid curve illustrates a constant exchange rate, resulting in a linear relationship between saturation and percent distance along the capillary from proximal end to distal end. The dashed and dotted-dashed curves illustrate more exponential-like relationships, with the dotted-dashed curve describing an exchange that results in over 90% of total oxygen extracted less than halfway across the capillary bed. Despite completely different kinetics, all three curves result in the same OEF. A multiple-inflow-time targeting approach, while increasing scan time, allows generation of these kinetic curves, revealing critical information about oxygen exchange dynamics not reflected in OEF alone.

This type of information is especially useful in disease states such as stroke and tumor and in situations of functional activation, in which oxygen exchange dynamics may be changing or unknown. Moreover, such information is also useful in expanding and improving current models of oxygen transport to tissue, many of which assume constant rates of exchange (like the solid curve in FIG. 9) and may be less physiologically accurate.

OEF and $CRMO_2$ maps can be used in various functional activation studies (fMRI) or clinical MRI. From a clinical standpoint, oxygen metabolism is a key indicator of tissue viability and functioning and is often affected early on in neuropathological states such as ischemic stroke and brain tumor. Accurate $CMRO_2$ maps allow for early detection of disease and, because of their quantitative nature, also allow longitudinal assessment of disease progression or response to therapy. Additionally, certain types and degrees of neuronal dysfunction may not affect $CMRO_2$, especially in early disease stages. Because OEF and $CMRO_2$ are based only on arterial and venous $SaO_2$, they focus more on the endpoints of oxygen exchange, but not the dynamics. A multiple-inflow-time targeting approach could instead be employed to uncover pathological changes in oxygen exchange kinetics that may not affect OEF or $CMRO_2$.

In an fMRI setting, $CMRO_2$ is purported to be a physiological property more tightly coupled (spatially and temporally) to neuronal activation compared to the more traditional forms of functional contrast, for example, blood flow and blood oxygen level dependence (BOLD). It may be a truer, more accurate surrogate for neuronal activation than these other forms of contrast and, if so, may be useful in studies attempting to elucidate brain structure and function. Additionally, absolute $CMRO_2$ maps and oxygen exchange dynamics would be of paramount importance in furthering our understanding of neurovascular coupling and the physiology behind brain activation and fMRI.

Therefore, the present invention provides an MR-based technique to isolate and target the MRI signal arising from specific vascular compartments in arterial, capillary, and venous circulation. By enabling such isolation and targeting, the isolated signal can be used to measure fundamental properties of brain physiology. For example, oxygen saturation ($SaO_2$), which is a compartment-specific physiological parameter, can be measured and used to calculate oxygen extraction fraction (OEF), cerebral metabolic rate of oxygen ($CMRO_2$), and oxygen exchange dynamics, on voxel-by-voxel basis.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:
1. A method of producing an image of a subject using an MRI system, the method comprising the steps of:
  a) directing the MRI system to perform a first pulse sequence that includes the following sequential steps:
    a1) applying a first velocity-selective pulse to suppress NMR signal from blood flowing faster than a first cutoff velocity through a plurality of vascular compartments of the subject;
    a2) providing an inflow time delay to allow blood to flow into selected vascular compartments of the plurality of vascular compartments;
    a3) applying a second velocity-selective pulse to suppress NMR signal from blood flowing faster than a second cutoff velocity through the plurality of vascular compartments;
  b) acquiring a tag set of NMR data from the subject after step a) and at a tag acquisition time after step a1);
  c) directing the MRI system to perform a second pulse sequence that includes the following sequential steps:
    c1) applying a third velocity-selective pulse to suppress NMR signal from blood flowing faster than a third cutoff velocity through the plurality of vascular compartments of the subject;
    c2) providing the inflow time delay to allow blood to flow into selected vascular compartments of the subject;
    c3) optionally applying a fourth velocity selective pulse to suppress NMR signal from blood flowing faster than a fourth cutoff velocity through the plurality of vascular compartments;
  d) acquiring a control set of NMR data from the subject after step c) and at a control acquisition time after step c1) that is equal to the tag acquisition time;
  e) reconstructing a tag image from the tag set of NMR data and a control image from the control set of NMR data; and
  f) subtracting the tag image from the control image to produce the image of the subject,
  wherein the third cutoff velocity and the fourth cutoff velocity are different velocities, and
  wherein the image of the subject indicates a characteristic of the blood flowing within the selected vascular compartments and is substantially free of information from both stationary tissue and blood outside the selected vascular compartments.

2. The method as recited in claim 1 wherein step a) includes applying an inversion pulse at a selected time during the inflow time delay to null recovering NMR signals.

3. The method as recited in claim 1 wherein the first velocity-selective pulse is spatially non-selective.

4. The method as recited in claim 1 further comprising the step of performing velocity bracketing to suppress NMR signal from blood having a velocity outside a selected velocity range.

5. The method as recited in claim 1 wherein step a3) includes eliminating signal from blood that has accelerated above the second cutoff velocity during the inflow time delay.

6. The method as recited in claim 1 wherein a physiological parameter is determined from the image that indicates a characteristics of the blood flowing within the selected vascular compartments.

7. The method as recited in claim 1 further including:
  e) i) reconstructing a series of tag and control images from the tag and control NMR data sets;
  f) i) performing a series of subtractions on tag and control image pairs to produce a series of subtraction images substantially free of information from both stationary tissues and moving blood outside the selected vascular compartments; and
  g) creating a mean subtraction image by averaging the subtraction images in the subtraction series.

8. The method as recited in claim 1 wherein step d) includes employing a spin-echo-based imaging module and steps e) and f) include generating images at multiple echo times.

9. The method as recited in claim 8 further comprising step h) creating $T_2$ maps specific to blood from the selected vascular compartments using the images at multiple echo times.

10. The method as recited in claim 9 wherein step h) includes measuring a physiological parameter from the $T_2$ maps specific to blood from the selected vascular compartments.

11. The method as recited in claim 1 wherein the characteristic is reflective of a physiological parameter including at least one of an oxygen extraction fraction (OEF), oxygen saturation ($SaO_2$), cerebral metabolic rate of oxygen ($CMRO_2$) partial pressure of oxygen ($PO_2$), kinetic curve of oxygen saturation, and kinetic curve of oxygen exchange.

12. The method as recited in claim 11 wherein the physiological parameter is generated on a voxel-by-voxel basis.

13. The method as recited in claim 1 wherein the characteristic of the blood flowing within the selected vascular compartments provides at least one indicator of oxygen exchange dynamics of the blood flowing within the selected vascular compartments.

14. A method of producing an image of a subject using an MRI system, the method comprising the steps of:
   a) directing the MRI system to perform a pulse sequence that includes the following sequential steps:
      a1) applying a first velocity-selective module configured to suppress NMR signal from blood flowing faster than a first cutoff velocity through a plurality of vascular compartments of the subject;
      a2) providing an inflow time delay to allow the blood to flow into selected vascular compartments of the plurality of vascular compartments;
      a3) applying a second velocity-selective module configured to suppress NMR signal from blood flowing faster than a second cutoff velocity through a plurality of vascular compartments of the subject;
   b) acquiring a tag set of NMR data from the subject after step a);
   c) directing the MRI system to perform a use sequence that includes the following sequential steps:
      c1) applying a third velocity-selective module configured to suppress NMR signal from blood flowing faster than a third cutoff velocity through a plurality of vascular compartments of the subject;
      c2) providing an inflow time delay to allow the blood to flow into selected vascular compartments of the plurality of vascular compartments;
      c3) applying a fourth velocity-selective module configured to suppress NMR signal from blood flowing faster than a fourth cutoff velocity through a plurality of vascular compartments of the subject, wherein the third cutoff velocity and the fourth cutoff velocity are different, non-zero velocities;
   d) acquiring a control set of NMR data from the subject after step c);
   e) reconstructing and subtracting the acquired tag set of NMR data and control set of NMR data to produce the image of the subject, wherein the image of the subject indicates a characteristics of oxygenation of the blood flowing within the selected vascular compartments and is free of information from both stationary tissue and blood outside the selected vascular compartments.

15. The method as recited in claim 14 wherein the control set of NMR data is acquired before the tag set of NMR data.

16. The method as recited in claim 14 wherein step e) includes reconstructing a tag image from the tag set of NMR data and a control image from the control set of NMR data and subtracting the tag image from the control image to produce the image of the subject.

17. The method as recited in claim 14 wherein step e) includes subtracting the tag NMR data set from the control NMR data set to produce a subtraction NMR data set and reconstructing the image of the subject from the subtraction NMR data set.

18. The method as recited in claim 14 wherein a physiological parameter is determined from the image that indicates characteristics of oxygenation of the blood flowing within the selected vascular compartments.

19. The method as recited in claim 14 wherein the first, second, third, and fourth cutoff velocities are different.

20. The method as recited in claim 14 wherein steps a) and b) include applying an inversion pulse at selected times during the respective inflow time delays to null recovering NMR signals.

21. The method as recited in claim 14 wherein the first velocity-selective pulse is spatially non-selective.

22. The method as recited in claim 14 further comprising the step of performing velocity bracketing to suppress NMR signal from blood having a velocity outside a selected velocity range.

23. The method as recited in claim 14 wherein steps b) and d) include employing a spin-echo-based imaging module and step e) includes generating compartment-specific images at multiple echo times.

24. The method as recited in claim 23 further comprising step f) creating $T_2$ maps specific to blood from the selected vascular compartments using the image that indicates a characteristics of oxygenation of the blood flowing within the selected vascular compartments.

25. The method as recited in claim 14 wherein the characteristic of oxygenation is at least one of an oxygen extraction fraction (OEF); oxygen saturation ($SaO_2$); cerebral rate of oxygen ($CMRO_2$); partial pressure of oxygen ($PO_2$); kinetic curve of oxygen saturation; and kinetic curve of oxygen exchange.

* * * * *

UNITED STATES PATENT AND TRADEMARK OFFICE
CERTIFICATE OF CORRECTION

PATENT NO. : 8,958,866 B2  
APPLICATION NO. : 12/413349  
DATED : February 17, 2015  
INVENTOR(S) : Divya S. Bolar et al.

Page 1 of 1

It is certified that error appears in the above-identified patent and that said Letters Patent is hereby corrected as shown below:

In the Claims

Column 12, line 55 - "char-acteristics" should be -- characteristic --

Column 13, line 41 - "use" should be -- pulse --

Column 14, line 6 - "characteristics" should be -- characteristic --

Column 14, line 45 - "char-acteristics" should be -- characteristic --

Signed and Sealed this  
Ninth Day of June, 2015

Michelle K. Lee  
*Director of the United States Patent and Trademark Office*